(12) United States Patent
Marshall et al.

(10) Patent No.: US 10,331,276 B2
(45) Date of Patent: Jun. 25, 2019

(54) PROJECTED INTERACTIVE DISPLAY SURFACE INTERACTIVITY DETERMINATION

(71) Applicants: Carl S. Marshall, Portland, OR (US); Selvakumar Panneer, Hillsboro, OR (US); Glen J. Anderson, Beaverton, OR (US); Meng Shi, Hillsboro, OR (US); Giuseppe Raffa, Portland, OR (US)

(72) Inventors: Carl S. Marshall, Portland, OR (US); Selvakumar Panneer, Hillsboro, OR (US); Glen J. Anderson, Beaverton, OR (US); Meng Shi, Hillsboro, OR (US); Giuseppe Raffa, Portland, OR (US)

(73) Assignee: Intel Corporation, Santa Clara, CA (US)

(*) Notice: Subject to any disclaimer, the term of this patent is extended or adjusted under 35 U.S.C. 154(b) by 164 days.

(21) Appl. No.: 15/396,136

(22) Filed: Dec. 30, 2016

(65) Prior Publication Data

US 2018/0188893 A1    Jul. 5, 2018

(51) Int. Cl.
*G06F 3/041*    (2006.01)
*G06F 3/042*    (2006.01)
(Continued)

(52) U.S. Cl.
CPC ............ *G06F 3/0426* (2013.01); *G01B 11/02* (2013.01); *G01B 11/14* (2013.01); *G01B 11/26* (2013.01);
(Continued)

(58) Field of Classification Search
CPC ...... G06F 3/042; G06F 3/0425; G06F 3/0426; G06F 3/048–3/04897; G01B 11/14;
(Continued)

(56) References Cited

U.S. PATENT DOCUMENTS 9,041,691 B1 *   5/2015   Haskin ................. G06F 3/0421
                                                345/175
9,478,067 B1 *  10/2016   Worley, III ........... G06F 3/0426
(Continued)

FOREIGN PATENT DOCUMENTS

KR    1020150080678 A    7/2015
KR    1020160144148 A   12/2016

OTHER PUBLICATIONS

International Search Report and Written Opinion for International Patent Application No. PCT/US2017/064636, dated Apr. 24, 2018, 13 pages.

*Primary Examiner* — Nathan Danielsen
(74) *Attorney, Agent, or Firm* — Jordan IP Law, LLC

(57) ABSTRACT

Apparatus and methods may provide for an interactive display projection with surface interactivity analysis. An interactive display projector is provided along with one or more of a camera or an electromagnetic radiation source to scan plural surfaces within a projection range of the interactive display projector. Logic, implemented at least partly in configurable or fixed functionality hardware may process reflected electromagnetic radiation to determine one or more of size, distance, texture, reflectivity, or angle with respect to the interactive display projector of the scanned plural surfaces and determine, based on the processing, interactivity of one or more of the plural surfaces for an interactive display.

20 Claims, 6 Drawing Sheets

(51) Int. Cl.
*G01B 11/02* (2006.01)
*G01B 11/14* (2006.01)
*G01B 11/26* (2006.01)
*G01N 21/55* (2014.01)

(52) U.S. Cl.
CPC ............ *G01N 21/55* (2013.01); *G06F 3/0418* (2013.01); *G01N 2201/12* (2013.01)

(58) Field of Classification Search
CPC ...... G01B 11/26–11/306; G01N 21/55; G01N 21/552–21/554; G01N 2021/551; G01N 2021/555–2021/559
See application file for complete search history.

(56) References Cited

U.S. PATENT DOCUMENTS

| | | | |
|---|---|---|---|
| 2008/0218641 | A1 | 9/2008 | Kjeldsen et al. |
| 2009/0313584 | A1* | 12/2009 | Kerr .................. G06F 3/012 715/849 |
| 2011/0063207 | A1 | 3/2011 | Lee |
| 2012/0182263 | A1 | 7/2012 | Lydegraf et al. |
| 2013/0229396 | A1* | 9/2013 | Huebner .............. G06F 3/0425 345/207 |
| 2014/0146304 | A1* | 5/2014 | Almalki ................ G01N 21/55 356/51 |
| 2014/0226167 | A1* | 8/2014 | Smith .................. G01B 11/14 356/614 |
| 2015/0338998 | A1 | 11/2015 | Chathoth et al. |
| 2017/0228104 | A1* | 8/2017 | Ziraknejad ............ G06F 3/0425 |

* cited by examiner

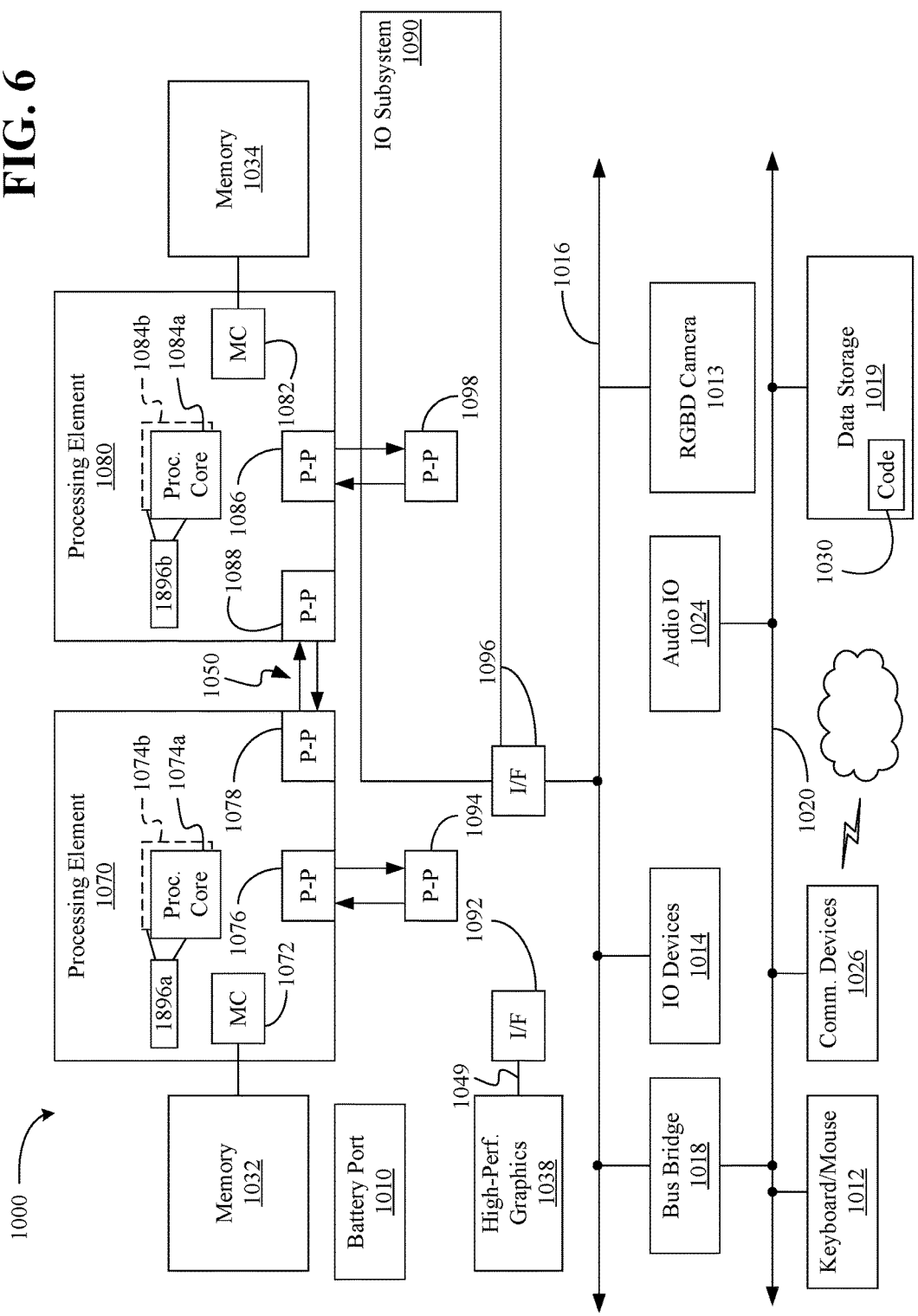

PROJECTED INTERACTIVE DISPLAY SURFACE INTERACTIVITY DETERMINATION

TECHNICAL FIELD

Embodiments generally relate to projected interactive displays and, more particularly, to determining surface interactivity for projected interactive displays.

BACKGROUND

Projected interactive displays may involve the projection of a display, which may be as complete as a graphical user interface or as simple as a keyboard image, onto a surface such as a wall or a table. A user may interact with the display through touch or gestures. The touch or gestures may be detected through a remote sensor and selections indicated by the touch or gestures may be analyzed to interactively change the display. For example, a touch of an icon may open a webpage or a gesture may enlarge a photo.

Within a given environment, such as a living room or a conference room, there may be many surfaces that are potential candidates onto which an interactive display may be projected. However, it may be difficult for a user to determine which surfaces possess interactivity for displays.

BRIEF DESCRIPTION OF THE DRAWINGS

The various advantages of the embodiments will become apparent to one skilled in the art by reading the following specification and appended claims, and by referencing the following drawings, in which:

FIG. 6 is a block diagram of an example of a computing system according to an embodiment.

DESCRIPTION OF EMBODIMENTS

Figure 1:
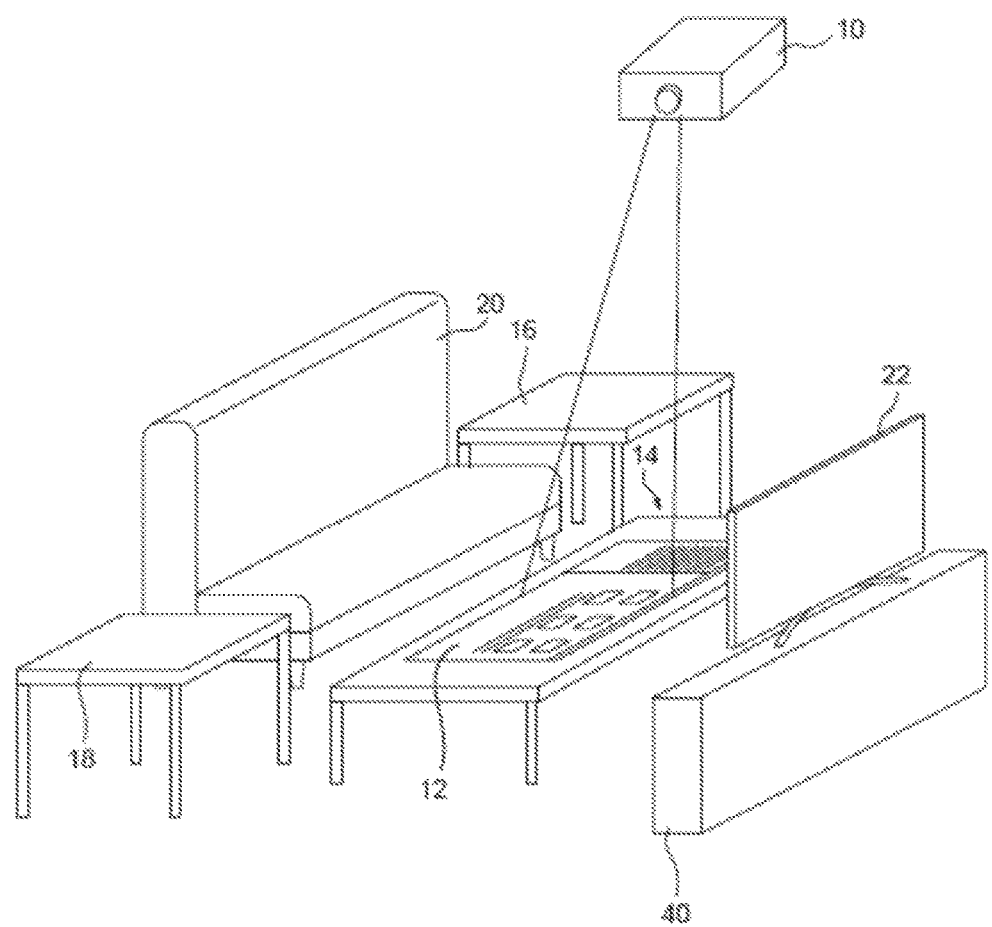
FIG. 1 is a perspective view of an example of a room having a projected interactive display.

Turning now to the drawings in detail, FIG. 1 depicts an example of a projected interactive display on a surface within a home. In FIG. 1, an interactive display projection system 10 projects an interactive display 12 onto a surface of a table 14. A user sitting on a sofa 20 may interact with the projected interactive display, for example, to open a web page and begin browsing. Further, the user may also view the interactive display on an optional display such as a television or a monitor 22. In this manner, a user may conveniently interact with a fixed, non-touchscreen display such as a monitor or television, without a peripheral such as a keyboard or mouse. Further, the projection of the interactive display on a surface near the user may be ergonomically advantageous. Projected interactive displays may also facilitate a more natural, three-dimensional interaction that can enhance a gaming experience.

A processing element 40 such as a computer may communicate with the interactive display projection system 10 and the optional display to analyze detected user touch or gestures and implement the user selections. Although the processing element 40 is depicted as a separate unit, it is understood that it may be integrated with the television or monitor 22. Further, the processing element 40 may be selected from a wide variety of devices with processing power including, but not limited to, mobile Internet devices (MIDs) such as smart phones and tablets, desktop computers, laptop computers, personal digital assistants, or any other device having processing power sufficient to analyze user touch or gestures. The processing element 40 may be integrated with the optional display as in a smart television, laptop computer, etc. Alternatively, the processing element 40 may be integrated with the interactive display projection system 10.

As seen in FIG. 1 plural surfaces may be present that are potential candidates for a projected interactive display. For example, the surfaces of tables 14, 16, and 18 are candidates as well as the surfaces of walls and floors of the depicted room. A user, however, may not know which of the plural surfaces are suited for interactivity from a perspective of size, distance, texture, reflectivity, or angle with respect to the interactive display projection system 10. As will be discussed in further detail below, the interactive display projection system 10 may analyze the plural surfaces in a room to determine the interactivity of surfaces on which an interactive display may be projected.

Figure 2:
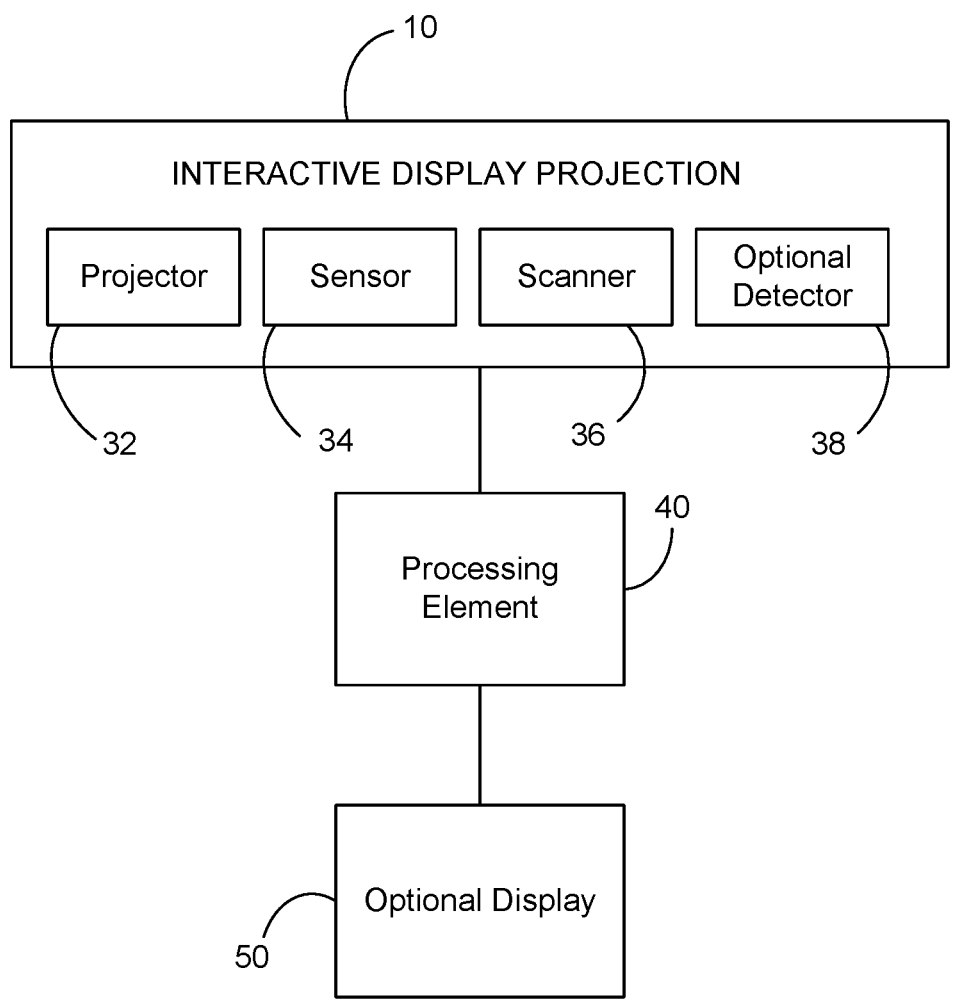
FIG. 2 is a block diagram of an example of a system according to an embodiment.

Turning to FIG. 2, an interactive display projection system 10 with surface interactivity analysis is schematically depicted. In one aspect, the interactive display projection system 10 includes a projector 32 to project an interactive display and a sensor 34 that analyzes touches and gestures of the user. The sensor 34 may be a depth camera such as a red-green-blue-depth (RGBD) camera. In one example of an RGBD camera, a near-infrared pulse is projected onto the object of interest. The reflected pulse is collected and, based on the known speed of light, the depth is determined by the amount of time for the pulse to return. In connection with the RGB color imaging, the returned pulse is integrated with a visual image. This type of RGBD camera may also be known as a "time of flight" camera due to the use of the time of flight of the near infrared pulse.

Although the sensor 34 is depicted as being co-located with the projector 32, the sensor 34 may be an independent unit and positioned elsewhere in the room in which the interactive display projection system 10 is located. In one aspect, a user may position the sensor 34 adjacent to the user to better capture touch and gestures as the user interacts with the projected display.

In a further aspect, the projection image may be less than a complete display. For example, a keyboard and/or touchpad may be projected for user interaction with a smart television. In the case of projected keyboards, an infrared beam may be projected in a region above the projected keyboard. The sensor 34 detects where the user's fingers break though the infrared beam when infrared light is reflected back to the sensor.

The interactive display projection system 10 may further include a scanner 36 to determine interactivity of plural surfaces for a projected interactive display. In one aspect, the scanner 36 may be a camera to scan the area of the room in which the interactive display projection system 10 is located. In another aspect, the scanner 36 may be an electromagnetic radiation source that puts out electromagnetic radiation to scan objects within the room. Electromagnetic radiation may include light, infrared, ultraviolet or any other portion of the electromagnetic spectrum that is capable of scanning objects within a room, An electromagnetic radiation source may be part of a lidar system (sometimes referred to as "light radar") to scan plural surfaces within the room. A lidar electromagnetic radiation source may be infrared, visible, or ultraviolet radiation. Laser radiation may be used to scan the room. The electromagnetic radiation may be backscattered from various surfaces to perform analysis of these surfaces.

When the scanner 36 is a camera, the camera may be an RGBD camera, as described above. In one aspect, the camera 36 may be eliminated and the sensor 34 may be used to analyze surface interactivity for interactive displays. When the scanner 36 is an electromagnetic radiation source an optional detector 38 is used to receive the backscattered radiation for determining various characteristics and thus interactivity of surfaces for interactive display projection. As set forth above, an RGBD camera itself can sense reflected electromagnetic radiation.

As depicted in FIG. 2, the scanner 36 and optional detector may be co-located with the projector 32. Alternatively, the scanner 36, the optional detector 38, or both may be positioned in one or more separate apparatus in the room or may be part of another system positioned in the room such as a smart home monitor. In other words, the interactive display projection system 10 may be an integrated unit as shown in FIG. 2 or it may comprise several apparatuses, each of which may include one or more of projector 32, sensor 34, scanner 36, and optional detector 38.

The projector 32, the sensor 34, the scanner 36 and the optional detector 38 may be in wired or wireless communication with the processing element 40. As described above, the processing element 40 may be a standalone processing element or it may be integrated with either the interactive display projection system 10 or integrated with the optional display 50. The processing element 40 may include logic, implemented at least partly in configurable or fixed functionality hardware, to perform the analysis of user touch and gestures and may also perform the analysis of surfaces to determine which of them possess interactivity for display projection. For example, the processing element 40 may perform segmenting of the various surfaces present in a room by depth analysis. When a region of an object has a substantially similar depth within an area followed by a large change in depth of surrounding areas, that region may be considered a single surface for the purpose of determining the interactivity of that surface for interactive display projection. In performing the analysis, the visual image (e.g., RGB image) may be compared to the depth data to segment surfaces. The size of the surface may also be determined through this same analysis. Depth also indicates the distance from the projector 32 to any surface. Through depth analysis the surface texture/roughness may be calculated to determine whether a surface is sufficiently smooth such that acceptable surface interactivity may be achieved.

A database of materials and their surface textures may be stored in the processing element 40 with an indication that certain surfaces are favored or not favored for interactivity with projected displays. For example, wood may be indicated by its surface texture and may be indicated as being a favorable surface for interactivity. A glass mirror or mirrored table may be indicated as an unfavorable surface for interactivity for some applications or through user feedback that may be stored in a database. Depending on user preferences, a particular user may find the interactivity of glass or mirrored surfaces to be sufficient and the database may include this information. Rough carpeted surfaces may be indicated as unfavorable for interactivity with certain displays due to uneven texture. However, for other applications, such as a musical keyboard that a user may jump on to create sound, rough carpeted surfaces may provide a reasonable surface interactivity level. Further, for "smart" devices within a room (e.g., a smart stove, smart refrigerator, objects that are part of the "Internet of Things" etc.), identification may be made by those devices through a wired or wireless connection to the processing element 40.

The processing element 40 may also determine reflectivity based on data from the scanner 36. Surface roughness combined with glare measurements (through brightness data) may provide an indication if an object surface is too reflective for good surface interactivity. A depth analysis may also indicate the angle of a surface with respect to the projector 32. The change in depth in a regular manner across a segmented region may indicate a surface that is at an angle other than normal to a lens of the projector 32. Depending upon the angle, the surface may or may not produce an image with good user interactivity. Typically angles that are close to normal will be acceptable. If there are multiple projectors within a room, the angles may be calculated with respect to the location of each projector and candidate surfaces will be indicated for each projector.

In one aspect, when the scanner 36 is an RGBD camera, the presence of a user may be detected through, for example, facial detection as determined by the processing element 40. By determining the location of a user, the distance from a user to potential candidate surfaces may be calculated and the results used to indicate which surfaces not only possess good interactivity but those which also are within reach of a user (e.g., are within a specified distance from the user).

In another aspect, a user may assist in determining whether a particular surface possesses good interactivity and/or assist in calibrating a display so that user touch and gestures may be accurately recognized by the processing element 40. For example, a calibration image may be displayed on a surface. A user may touch a calibration point on the surface to determine the presence of jitter where the calibration point aligns with a point on the display 50. This may be performed with multiple calibration points. The user may also perform a gesture such as a swipe to evaluate if multiple points along the swipe path are detected or if skipping occurred. In one aspect, a calibration image may be displayed through a picture-in-picture on the display 50. During calibration, a user may adjust the borders of a projected image by dragging the corners to map the touch region to a display region on display 50. In another aspect, all the surfaces with good interactivity are indicated either simultaneously or sequentially to a user. The user may then select the desired surface for the display through touch or gesture.

The processing element 40 may communicate through a wired or wireless connection to the optional display 50. The processing element 40 may include logic, implemented at least partly in configurable or fixed functionality hardware that analyzes the touch or gestures of a user and causes display events to appear on both the optional display 50 as well as the projected display. The processing element further analyzes the various features described above such as size, distance, texture, reflectivity or angle with respect to the projector, and determines which surfaces have interactivity for an interactive display projection. The processing element 40 may optionally take in account the detected position of a user in making the determination.

Figure 3:
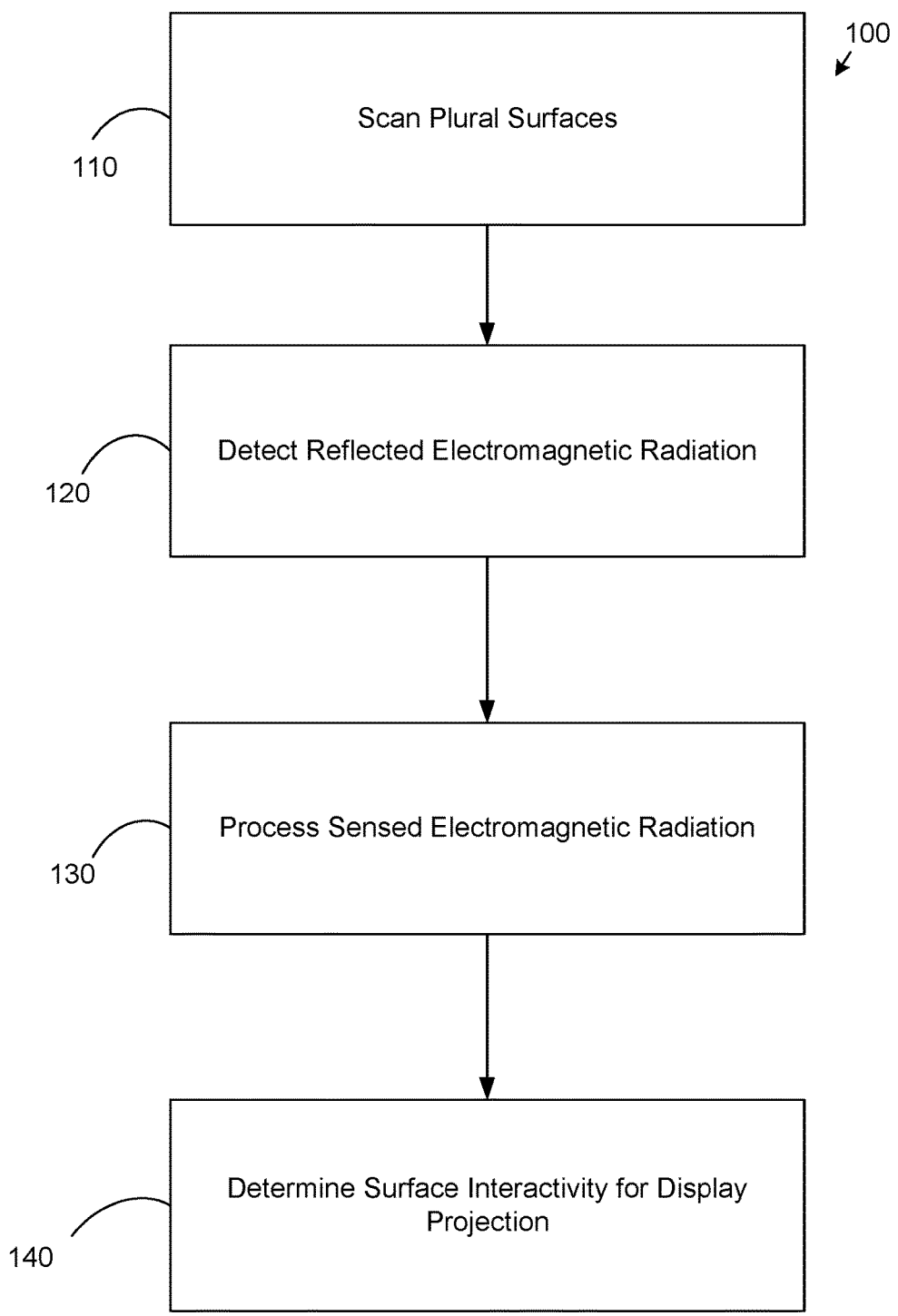
FIG. 3 is a flowchart of an example of a method of operating a surface interactivity determination apparatus according to an embodiment.

FIG. 3 shows an overview of a method 100 of operating a surface interactivity determination apparatus. The method 100 may generally be implemented in an interactive display projection system such as, for example, the interactive display projection system 10 including processing element 40 (FIG. 2), already discussed. More particularly, the method 100 may be implemented in one or more modules as a set of logic instructions stored in a machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality logic hardware using circuit technology such as, for example, application specific integrated circuit (ASIC), complementary metal oxide semiconductor (CMOS) or transistor-transistor logic (TTL) technology, or any combination thereof. For example, computer program code to carry out operations shown in method 100 may be written in any combination of one or more programming languages, including an object oriented programming language such as JAVA, SMALLTALK, C++ or the like and conventional procedural programming languages, such as the "C" programming language or similar programming languages.

Illustrated processing block 110 provides for scanning plural surfaces within a projection range of an interactive display projector with one or more of a camera or electromagnetic radiation. Some cameras, such as an RGBD camera, scan both for images of objects and also send out scanning electromagnetic radiation which is used for determining the depth of the images. The plural surfaces may then reflect the scanned electromagnetic radiation. Alternatively, the plural surfaces may reflect ambient incident electromagnetic radiation such as light.

In processing block 120, an optional detector or an RGBD camera detects reflected electromagnetic radiation from the scanned plural surfaces. An RGBD camera may use a CMOS sensor to detect reflected electromagnetic radiation and integrate the information with image information from an RGB pixel.

In processing block 130, the sensed electromagnetic radiation is processed to determine one or more of size, distance, angle with respect to the interactive display projector, texture, or reflectivity of the scanned plural surfaces. A processing element, such as processing element 40 which may be a standalone element or integrated into a projection system or optional display system, processes the sensed electromagnetic radiation to determine the above characteristics.

In processing block 140, interactivity of one or more of the plural surfaces is determined based on the processing. This determination may include consideration of the location of the user, the angles at which a projector may be able to create a display, whether the size of a surface may is sufficient for a display that is readable by a user (e.g., font size that is able to be read, icon size, etc.), whether reflectivity is too high for a display to appear (that is, would incident light from the display be reflected back, rendering the display unreadable), touchability of the surface based on measured surface texture, etc.

Optionally, the method may include altering environmental factors to improve interactivity of surfaces for interactive display projection. For example, light sources in a room may be turned off or blinds may be drawn to decrease the reflectivity of one or more surfaces. The method may also include user feedback such as the user feedback described above with respect to calibration of a projected display. Further the user may select a particular surface when plural surfaces have sufficient interactivity.

Figure 4:
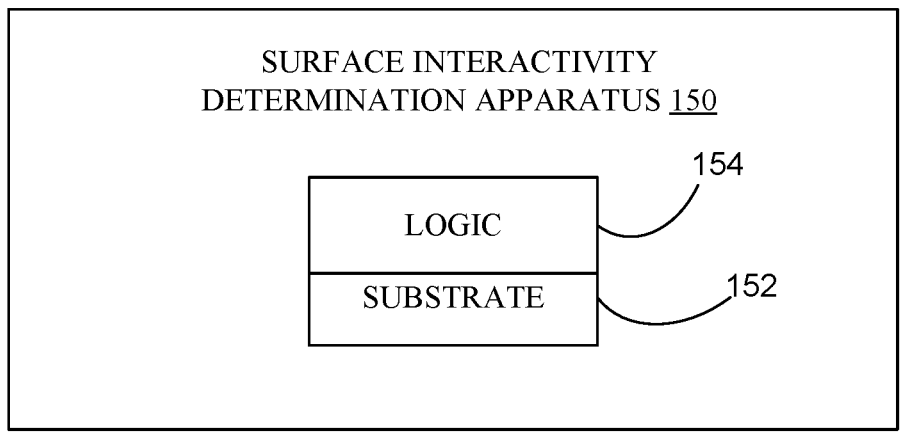
FIG. 4 is a block diagram of an example of an apparatus according to an embodiment.

FIG. 4 shows a surface interactivity determination apparatus 150. The apparatus 150 may implement one or more aspects of the method 100 (FIG. 3) and may be employed in the interactive display projection system 10 (FIG. 1), already discussed. The illustrated apparatus 150 includes a substrate 152 (e.g., silicon, sapphire, gallium arsenide) and logic 154 (e.g., transistor array and other integrated circuit/IC components) coupled to the substrate 152. The logic 154 may be implemented at least partly in configurable logic or fixed-functionality logic hardware. Moreover, the logic 154 may process reflected electromagnetic radiation to determine one or more of size, distance, texture, reflectivity, or angle with respect to an interactive display projector of the scanned plural surfaces and determine, based on the processing, the interactivity of the plural surfaces for interactive display.

The processing element 40 may include a processor, such as a processor including the processor core of FIG. 4. FIG. 4 illustrates a processor core 200 according to one embodiment. The processor core 200 may be the core for any type of processor, such as a micro-processor, an embedded processor, a digital signal processor (DSP), a network processor, a graphics processing unit, or other device to execute code. Although only one processor core 200 is illustrated in FIG. 4, a processing element may alternatively include more than one of the processor core 200 illustrated in FIG. 4. The processor core 200 may be a single-threaded core or, for at least one embodiment, the processor core 200 may be multithreaded in that it may include more than one hardware thread context (or "logical processor") per core.

FIG. 4 also illustrates a memory 270 coupled to the processor core 200. The memory 270 may be any of a wide variety of memories (including various layers of memory hierarchy) as are known or otherwise available to those of skill in the art. The memory 270 may include one or more code 213 instruction(s) to be executed by the processor core 200, wherein the code 213 may implement the method 20 (FIG. 3), already discussed. The processor core 200 follows a program sequence of instructions indicated by the code 213. Each instruction may enter a front end portion 210 and be processed by one or more decoders 220. The decoder 220 may generate as its output a micro operation such as a fixed width micro operation in a predefined format, or may generate other instructions, microinstructions, or control signals which reflect the original code instruction. The illustrated front end portion 210 also includes register renaming logic 225 and scheduling logic 230, which generally allocate resources and queue the operation corresponding to the convert instruction for execution.

The processor core 200 is shown including execution logic 250 having a set of execution units 255-1 through 255-N. Some embodiments may include a number of execution units dedicated to specific functions or sets of functions. Other embodiments may include only one execution unit or one execution unit that can perform a particular function. The illustrated execution logic 250 performs the operations specified by code instructions.

After completion of execution of the operations specified by the code instructions, back end logic 260 retires the instructions of the code 213. In one embodiment, the processor core 200 allows out of order execution but requires in order retirement of instructions. Retirement logic 265 may take a variety of forms as known to those of skill in the art (e.g., re-order buffers or the like). In this manner, the processor core 200 is transformed during execution of the code 213, at least in terms of the output generated by the decoder, the hardware registers and tables utilized by the register renaming logic 225, and any registers (not shown) modified by the execution logic 250.

Although not illustrated in FIG. 4, a processing element may include other elements on chip with the processor core 200. For example, a processing element may include memory control logic along with the processor core 200. The processing element may include I/O control logic and/or may include I/O control logic integrated with memory control logic. The processing element may also include one or more caches.

Figure 5:
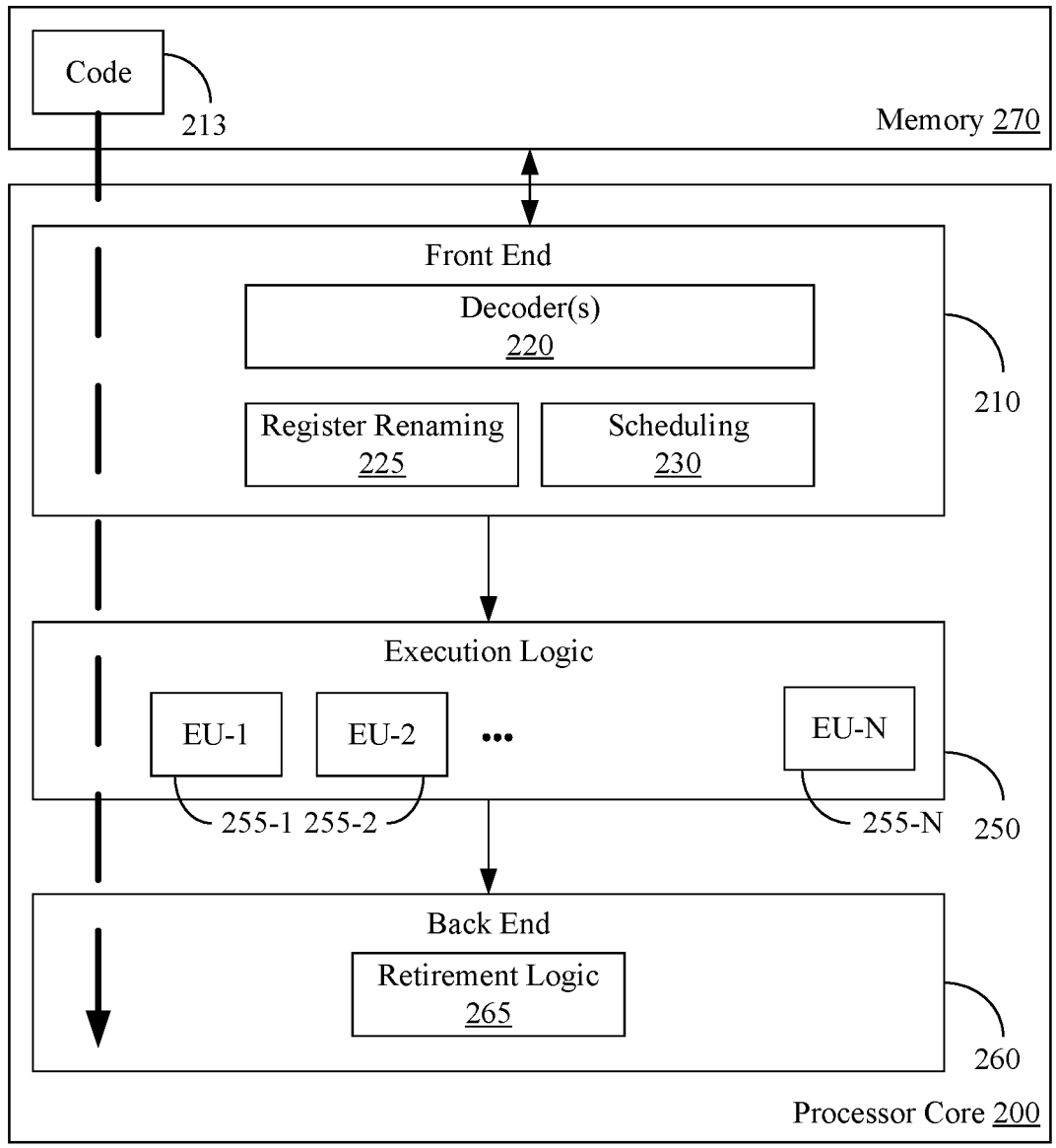
FIG. 5 is a block diagram of an example of a processor according to an embodiment.

Referring now to FIG. 5, shown is a block diagram of a computing system 1000 in accordance with an embodiment. Shown in FIG. 5 is a multiprocessor system 1000 that includes a first processing element 1070 and a second processing element 1080. While two processing elements 1070 and 1080 are shown, it is to be understood that an embodiment of the system 1000 may also include only one such processing element.

The system 1000 is illustrated as a point-to-point interconnect system, wherein the first processing element 1070 and the second processing element 1080 are coupled via a point-to-point interconnect 1050. It should be understood that any or all of the interconnects illustrated in FIG. 5 may be implemented as a multi-drop bus rather than point-to-point interconnect.

As shown in FIG. 5, each of processing elements 1070 and 1080 may be multicore processors, including first and second processor cores (i.e., processor cores 1074a and 1074b and processor cores 1084a and 1084b). Such cores 1074a, 1074b, 1084a, 1084b may be configured to execute instruction code in a manner similar to that discussed above in connection with FIG. 4.

Each processing element 1070, 1080 may include at least one shared cache 1896a, 1896b. The shared cache 1896a, 1896b may store data (e.g., instructions) that are utilized by one or more components of the processor, such as the cores 1074a, 1074b and 1084a, 1084b, respectively. For example, the shared cache 1896a, 1896b may locally cache data stored in a memory 1032, 1034 for faster access by components of the processor. In one or more embodiments, the shared cache 1896a, 1896b may include one or more mid-level caches, such as level 2 (L2), level 3 (L3), level 4 (L4), or other levels of cache, a last level cache (LLC), and/or combinations thereof.

While shown with only two processing elements 1070, 1080, it is to be understood that the scope of the embodiments are not so limited. In other embodiments, one or more additional processing elements may be present in a given processor. Alternatively, one or more of processing elements 1070, 1080 may be an element other than a processor, such as an accelerator or a field programmable gate array. For example, additional processing element(s) may include additional processors(s) that are the same as a first processor 1070, additional processor(s) that are heterogeneous or asymmetric to processor a first processor 1070, accelerators (such as, e.g., graphics accelerators or digital signal processing (DSP) units), field programmable gate arrays, or any other processing element. There can be a variety of differences between the processing elements 1070, 1080 in terms of a spectrum of metrics of merit including architectural, micro architectural, thermal, power consumption characteristics, and the like. These differences may effectively manifest themselves as asymmetry and heterogeneity amongst the processing elements 1070, 1080. For at least one embodiment, the various processing elements 1070, 1080 may reside in the same die package.

The first processing element 1070 may further include memory controller logic (MC) 1072 and point-to-point (P-P) interfaces 1076 and 1078. Similarly, the second processing element 1080 may include a MC 1082 and P-P interfaces 1086 and 1088. As shown in FIG. 6, MC's 1072 and 1082 couple the processors to respective memories, namely a memory 1032 and a memory 1034, which may be portions of main memory locally attached to the respective processors. While the MC 1072 and 1082 is illustrated as integrated into the processing elements 1070, 1080, for alternative embodiments the MC logic may be discrete logic outside the processing elements 1070, 1080 rather than integrated therein.

The first processing element 1070 and the second processing element 1080 may be coupled to an I/O subsystem 1090 via P-P interconnects 1076 1086, respectively. As shown in FIG. 5, the I/O subsystem 1090 includes P-P interfaces 1094 and 1098. Furthermore, I/O subsystem 1090 includes an interface 1092 to couple I/O subsystem 1090 with a high performance graphics engine 1038. In one embodiment, bus 1049 may be used to couple the graphics engine 1038 to the I/O subsystem 1090. Alternately, a point-to-point interconnect may couple these components.

In turn, I/O subsystem 1090 may be coupled to a first bus 1016 via an interface 1096. In one embodiment, the first bus 1016 may be a Peripheral Component Interconnect (PCI) bus, or a bus such as a PCI Express bus or another third generation I/O interconnect bus, although the scope of the embodiments are not so limited.

As shown in FIG. 5, various I/O devices 1014 (e.g., speakers, cameras, sensors) may be coupled to the first bus 1016, along with a bus bridge 1018 which may couple the first bus 1016 to a second bus 1020. In one embodiment, the second bus 1020 may be a low pin count (LPC) bus. Various devices may be coupled to the second bus 1020 including, for example, a keyboard/mouse 1012, communication device(s) 1026, an RGBD camera 1013 (which may be the scanner 36 of FIG. 2) and a data storage unit 1019 such as a disk drive or other mass storage device which may include code 1030, in one embodiment. The illustrated code 1030, which may be similar to the code 213 (FIG. 4), may implement the method 100 (FIG. 3), already discussed. Further, an audio I/O 1024 may be coupled to second bus 1020 and a battery 1010 may supply power to the computing system 1000.

Note that other embodiments are contemplated. For example, instead of the point-to-point architecture of FIG. 5, a system may implement a multi-drop bus or another such communication topology. Also, the elements of FIG. 5 may alternatively be partitioned using more or fewer integrated chips than shown in FIG. 5.

Additional Notes and Examples

Example 1 may include an interactive display projection system comprising an interactive display projector, one or more of a camera or an electromagnetic radiation source to scan plural surfaces within a projection range of the interactive display projector, logic, implemented at least partly in configurable or fixed functionality hardware to: process data corresponding to reflected electromagnetic radiation to determine one or more of size, distance, texture, reflectivity, or angle with respect to the interactive display projector of the scanned plural surfaces, and determine, based on processing the reflected electromagnetic radiation, interactivity of one or more of the plural for interactive display.

Example 2 may include the system of example 1, comprising a camera.

Example 3 may include the system of example 2, wherein the camera is an RGBD camera.

Example 4 may include the system of example 1, comprising a radiation source.

Example 5 may include the system of example 4, further comprising a radiation detector.

Example 6 may be a surface determination apparatus including a substrate, logic, coupled to the substrate and implemented at least partly in configurable or fixed functionality hardware to conduct an analysis of data corresponding to reflected electromagnetic radiation to determine one or more of size, texture, distance, reflectivity, or angle with respect scanned plural surfaces within a projection range of an interactive display projector, and determine, based on the analysis, interactivity of one or more of the plural surfaces for interactive display.

Example 7 may include the apparatus of example 6, further comprising a camera.

Example 8 may include the apparatus of example 7, wherein the camera is an RGBD camera Example 9 may include the apparatus of example 6, further comprising a radiation source.

Example 10 may include the apparatus of example 9, further comprising a radiation detector.

Example 11 may include a method of operating a surface determination apparatus comprising scanning plural surfaces within a projection range of an interactive display projector with one or more of a camera or electromagnetic radiation, detecting reflected electromagnetic radiation from the scanned plural surfaces, processing the sensed electromagnetic radiation to determine one or more of size, distance, angle with respect to the interactive display projector, texture, or reflectivity of the scanned plural surfaces, and determining, based on the processing, interactivity of one or more of the plural surfaces for an interactive display.

Example 12 may include the method of example 11, further comprising adjusting ambient light to change reflectivity of one or more of the plural surfaces.

Example 13 may include the method of examples 11 or 12, wherein the scanning is conducted with a camera.

Example 14 may include the method of example 13, wherein the camera is an RGBD camera.

Example 15 may include the method of example 11, further comprising notifying a user regarding which of the plural surfaces possesses interactivity for an interactive display.

Example 16 may include a non-transitory computer readable storage medium comprising a set of instructions which, when executing by a processor, cause an interactive display projection system to scan plural surfaces within a projection range of an interactive display projector with one or more of a camera or electromagnetic radiation, detect reflected electromagnetic radiation from the scanned plural surfaces, processing the sensed electromagnetic radiation to determine one or more of size, distance, angle with respect to the interactive display projector, texture, or reflectivity of the scanned plural surfaces, and determine, based on the processing, interactivity of one or more of the plural surfaces for an interactive display.

Example 17 may include the medium of example 16, wherein the instructions, when executed, cause the interactive display projection system to adjust ambient light to change reflectivity of one or more of the plural surfaces.

Example 18 may include the medium of example 16, wherein the scanning is to be conducted with a camera.

Example 19 may include the medium of example 18, wherein the camera is an RGBD camera.

Example 20 may include the medium of any of examples 16-19, wherein the instructions, when executed, cause the interactive display projection system to notify a user regarding which of the plural surfaces possesses interactivity for an interactive display.

Example 21 may include an apparatus to analyze surfaces for a projected interactive display comprising means for scanning plural surfaces within a projection range of an interactive display projector with one or more of a camera or electromagnetic radiation, means for detecting reflected electromagnetic radiation from the scanned plural surfaces, means for processing the reflected electromagnetic radiation to determine one or more of size, distance, angle with respect to the interactive display projector, texture, or reflectivity of the scanned plural surfaces, and means for determining, based on the processing, interactivity of one or more of the plural surfaces for an interactive display.

Example 22 may include the apparatus of example 21, further comprising adjusting ambient light to change reflectivity of one or more of the plural surfaces.

Example 23 may include the apparatus of example 21, wherein the scanning is to be conducted with a camera.

Example 24 may include the apparatus of example 23, wherein the camera is an RGBD camera.

Example 25 may include the apparatus of any of examples 21-24, further comprising notifying a user regarding which of the plural surfaces possesses interactivity for an interactive display.

Embodiments are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD/NAND controller ASICs, and the like. In addition, in some of the drawings, signal conductor lines are represented with lines. Some may be different, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments, it should be apparent to one skilled in the art that embodiments can be practiced without, or with variation of, these specific details. The description is thus to be regarded as illustrative instead of limiting.

The terms "coupled" and "communicating" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

Those skilled in the art will appreciate from the foregoing description that the broad techniques of the embodiments can be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

We claim:

1. A system comprising:
an interactive display projector;
one or more of a camera or an electromagnetic radiation source to scan plural surfaces within a projection range of the interactive display projector; and
logic, implemented at least partly in configurable logic or fixed functionality logic hardware, to:
process data corresponding to reflected electromagnetic radiation to determine one or more of size, distance, texture, angle with respect to the interactive display projector or reflectivity of the scanned plural surfaces;
determine, based on processing of the reflected electromagnetic radiation, interactivity of one or more surfaces of the scanned plural surfaces for an interactive display; and
determine that at least one surface of the one or more surfaces is to be excluded from having the interactive display projected onto the at least one surface based on the determined interactivity.

2. The system of claim 1, further comprising the camera.

3. The system of claim 2, wherein the camera is a red-green-blue-depth camera.

4. The system of claim 1, further comprising:
the electromagnetic radiation source; and
a radiation detector.

5. An apparatus comprising:
a substrate; and
logic, coupled to the substrate and implemented at least partly in configurable logic or fixed functionality logic hardware, to:
conduct an analysis of data corresponding to reflected electromagnetic radiation to determine one or more of size, texture, distance, angle with respect to an interactive display projector or reflectivity of scanned plural surfaces within a projection range of the interactive display projector;
determine, based on the analysis, interactivity of one or more surfaces of the scanned plural surfaces for an interactive display and
determine that at least one surface of the one or more surfaces is to be excluded from having the interactive display projected onto the at least one surface based on the determined interactivity.

6. The apparatus of claim 5, further comprising a camera.

7. The apparatus of claim 6, wherein the camera is a red-green-blue-depth camera.

8. The apparatus of claim 5, further comprising:
a radiation source; and
a radiation detector.

9. A method comprising:
scanning plural surfaces within a projection range of an interactive display projector;
detecting reflected electromagnetic radiation from the scanned plural surfaces;
processing the reflected electromagnetic radiation to determine one or more of size, distance, angle with respect to the interactive display projector, texture, or reflectivity of the scanned plural surfaces;
determining, based on the processing, interactivity of one or more surfaces of the scanned plural surfaces for an interactive display; and
determining that at least one surface of the one or more surfaces is to be excluded from having the interactive display projected onto the at least one surface based on the determined interactivity.

10. The method of claim 9, further comprising adjusting ambient light to change reflectivity of one or more of the scanned plural surfaces.

11. The method of claim 9, wherein the scanning is conducted with a camera.

12. The method of claim 11, wherein the camera is a red-green-blue-depth camera.

13. The method of claim 9, further comprising notifying a user regarding which of the scanned plural surfaces possesses interactivity for the interactive display.

14. A non-transitory computer readable storage medium comprising a set of instructions which, when executing by a processor, cause an interactive display projection system to:
scan plural surfaces within a projection range of an interactive display projector with one or more of a camera or an electromagnetic radiation source;
detect reflected electromagnetic radiation from the scanned plural surfaces;
conduct an analysis of the reflected electromagnetic radiation to determine one or more of size, distance, angle with respect to the interactive display projector, texture, or reflectivity of the scanned plural surfaces;
determine, based on the analysis, interactivity of one or more surfaces of the scanned plural surfaces for an interactive display; and
determine that at least one surface of the one or more surfaces is to be excluded from having the interactive display projected onto the at least one surface based on the determined interactivity.

15. The medium of claim 14, wherein the instructions, when executed, cause the interactive display projection system to adjust ambient light to change reflectivity of one or more of the scanned plural surfaces.

16. The medium of claim 14, wherein the scanning is to be conducted with a red-green-blue-depth camera.

17. The medium of claim 14, wherein the instructions, when executed, cause the interactive display projection system to notify a user regarding which of the scanned plural surfaces possesses interactivity for the interactive display.

18. The medium of claim 14, wherein the instructions, when executed, cause the interactive display projection system to:
determine one or more of a surface texture or roughness of a first surface from the scanned plural surfaces; and
identify that the interactive display is to be projected onto the first surface based on the one or more of the surface texture or the roughness being identified as acceptable for surface interactivity.

19. The medium of claim 14, wherein the instructions, when executed, cause the interactive display projection system to:
- determine a reflectivity of a first surface from the scanned plural surfaces; and
- identify that the interactive display is to be projected onto the first surface based on the reflectivity of the first surface being identified as acceptable for surface interactivity.

20. The medium of claim 14, wherein the instructions, when executed, cause the interactive display projection system to:
- determine that the at least one surface is to be excluded from having the interactive display projected onto the at least one surface based on an identification that the at least one surface is outside of a specified distance from a user.

* * * * *